United States Patent
Nakanishi et al.

(10) Patent No.: US 12,114,830 B2
(45) Date of Patent: Oct. 15, 2024

(54) MEDICAL CONTROL APPARATUS AND MEDICAL OBSERVATION SYSTEM

(71) Applicant: Sony Olympus Medical Solutions Inc., Tokyo (JP)

(72) Inventors: Tatsuya Nakanishi, Tokyo (JP); Takamasa Mikami, Tokyo (JP); Takahiro Tamura, Tokyo (JP)

(73) Assignee: Sony Olympus Medical Solutions Inc., Tokyo (JP)

(*) Notice: Subject to any disclaimer, the term of this patent is extended or adjusted under 35 U.S.C. 154(b) by 159 days.

(21) Appl. No.: 17/137,381

(22) Filed: Dec. 30, 2020

(65) Prior Publication Data
US 2021/0228065 A1    Jul. 29, 2021

(30) Foreign Application Priority Data
Jan. 29, 2020   (JP) .................. 2020-012939

(51) Int. Cl.
*A61B 1/00* (2006.01)
*A61B 1/06* (2006.01)

(52) U.S. Cl.
CPC .... *A61B 1/00006* (2013.01); *A61B 1/000095* (2022.02); *A61B 1/00126* (2013.01); *A61B 1/00194* (2022.02); *A61B 1/0605* (2022.02); *A61B 1/0655* (2022.02); *A61B 1/0661* (2013.01)

(58) Field of Classification Search
CPC .......... A61B 1/00006; A61B 1/000095; A61B 1/0605; A61B 1/00194; A61B 1/0655; A61B 1/00126; A61B 1/0661
See application file for complete search history.

(56) References Cited

U.S. PATENT DOCUMENTS

| 5,006,848 | A | * | 4/1991 | Fukumizu | ............... G01D 5/25 341/15 |
| 5,797,836 | A | * | 8/1998 | Lucey | ...................... A61B 1/05 600/173 |
| 6,464,633 | B1 | * | 10/2002 | Hosoda | .............. G02B 23/2469 348/69 |

(Continued)

FOREIGN PATENT DOCUMENTS

| JP | H02208513 A | 8/1990 |
| JP | H08332169 A | 12/1996 |

(Continued)

OTHER PUBLICATIONS

Japanese Decision to Grant issued Dec. 26, 2023, in corresponding Japanese Patent Application No. 2020-012939, 5 pp.

*Primary Examiner* — John P Leubecker
*Assistant Examiner* — Li-Ting Song
(74) *Attorney, Agent, or Firm* — XSENSUS LLP

(57) ABSTRACT

A medical control apparatus includes a circuitry configured to: generate an irradiation image represented by illuminating-light irradiation, based on a brightness distribution of a captured image captured by an imaging device; and control generation of a projection image and projection of the projection image onto a subject by an image projector provided in an optical member based on the irradiation image and a rotation angle for rotation of the optical member rotatably coupled to the imaging device about a longitudinal axis of the optical member relative to the imaging device.

19 Claims, 12 Drawing Sheets

(56) References Cited

U.S. PATENT DOCUMENTS

| | | | |
|---|---|---|---|
| 7,387,605 B2* | 6/2008 | Frith | A61B 1/042 600/137 |
| 2006/0206003 A1* | 9/2006 | Hoeg | G02B 27/642 600/117 |
| 2006/0229495 A1* | 10/2006 | Frith | A61B 1/00126 600/112 |
| 2013/0278738 A1* | 10/2013 | Hayashi | A61B 1/00009 348/68 |
| 2014/0066710 A1* | 3/2014 | Graves | A61B 1/00066 600/117 |
| 2014/0221749 A1* | 8/2014 | Grant | A61B 1/126 600/109 |
| 2014/0285644 A1* | 9/2014 | Richardson | A61B 1/00006 348/68 |
| 2017/0095144 A1* | 4/2017 | Tabata | A61B 1/06 |
| 2017/0143191 A1* | 5/2017 | Haraguchi | A61B 1/00154 |
| 2017/0224205 A1* | 8/2017 | Sunar | A61B 1/0684 |
| 2017/0290498 A1* | 10/2017 | Tamura | F21V 9/45 |
| 2018/0263474 A1* | 9/2018 | Imade | A61B 1/045 |
| 2018/0310812 A1* | 11/2018 | Kuriyama | A61B 1/00188 |
| 2019/0208986 A1* | 7/2019 | Saito | A61B 1/000094 |
| 2020/0113425 A1* | 4/2020 | Ito | G02B 23/26 |
| 2021/0208383 A1* | 7/2021 | Yamazaki | G02B 23/2461 |
| 2024/0172931 A1* | 5/2024 | Bormet | A61B 1/045 |

FOREIGN PATENT DOCUMENTS

| | | |
|---|---|---|
| JP | 2001078960 A | 3/2001 |
| JP | 2003290119 A | 10/2003 |
| JP | 2012249757 A | 12/2012 |
| WO | WO-2014156217 A1 | 10/2014 |
| WO | 2015/001806 A1 | 1/2015 |
| WO | WO-2017168986 A1 | 10/2017 |
| WO | WO-2018061390 A1 | 4/2018 |
| WO | WO-2018235166 A1 | 12/2018 |
| WO | WO-2019239942 A1 | 12/2019 |

* cited by examiner

MEDICAL CONTROL APPARATUS AND MEDICAL OBSERVATION SYSTEM

CROSS-REFERENCE TO RELATED APPLICATION

This application claims priority from Japanese Application No. 2020-012939, filed on Jan. 29, 2020, the contents of which are incorporated by reference herein in its entirety.

BACKGROUND

The present disclosure relates to a medical observation system.

In a medical field and an industrial field, there have been known medical apparatuses such as an endoscope apparatus that captures a subject image using an imaging element and a medical microscope apparatus (refer to JP 2002-159445 A, for example). Among such medical apparatuses, an endoscope apparatus includes an endoscope, an imaging device, a display device, a control device, and a light source device, for example. In such an endoscope apparatus, illuminating light is supplied from a light source device via a light guide connected to an endoscope and a subject image is captured by illuminating-light irradiation.

In observing a three-dimensional structure using an endoscope, depending on the shape of irregularities in a surface of the structure, too light areas or too dark areas are locally produced because of lack of balance between brightness at a near point and brightness at a far point in some cases. In a light source device disclosed in JP 2002-159445 A, which includes a plurality of LED light sources, a quantity of light emitted from each of the LED light sources is controlled, thereby changing a light-quantity distribution of light emitted from the light source device. By controlling a light-quantity distribution, it is possible to regulate a local difference in brightness between a near point and a far point.

On the other hand, as a technique for emitting light having a predetermined irradiation pattern from an endoscope, there has been described a configuration that measures a three-dimensional shape of a surface of a subject (refer to JP 2012-242364 A, for example). According to JP 2012-242364 A, a stripe pattern formed of alternating light and dark bands is projected, and a plurality of images are acquired by phase shift of the stripe pattern. Then, based on the acquired images, the three-dimensional shape is measured.

SUMMARY

With regard to JP 2002-159445 A, there is a limit to a controllable light-quantity distribution in a single LED light source. Further, JP 2012-242364 A is directed to a pattern for measuring a three-dimensional shape of a subject and is not directed to setting of an irradiation pattern in accordance with the shape of a subject. Thus, there has been a demand for a technique of regulating a light-quantity distribution more finely to make an image of a complicated three-dimensional structure clear.

According to one aspect of the present disclosure, there is provided a medical control apparatus including a circuitry configured to: generate an irradiation image represented by illuminating-light irradiation, based on a brightness distribution of a captured image captured by an imaging device; and control generation of a projection image and projection of the projection image onto a subject by an image projector provided in an optical member based on the irradiation image and a rotation angle for rotation of the optical member rotatably coupled to the imaging device about a longitudinal axis of the optical member relative to the imaging device.

According to another aspect of the present disclosure, there is provided a medical observation system including: an optical member having an elongated shape, the optical member being configured to condense a subject image and emit supplied light from a distal end; an imaging device coupled to the optical member such that the optical member is removable and rotatable about a longitudinal axis of the optical member, the imaging device being configured to capture the subject image condensed by the optical member; circuitry configured to generate a captured image based on an electric signal generated through capture by the imaging device, detect a rotation angle of the optical member for rotation about the longitudinal axis relative to the imaging device, generate an irradiation image that indicates a distribution of a light quantity of illumination light based on a distribution of the light quantity in accordance with a brightness distribution of the captured image, correct the irradiation image in accordance with the rotation angle; a light source configured to supply light to the optical member; and an image projector provided in the optical member, the image projector being configured to generate a projection image based on the irradiation image having been corrected by the circuitry and project the projection image onto a subject.

DETAILED DESCRIPTION

Figure 1:
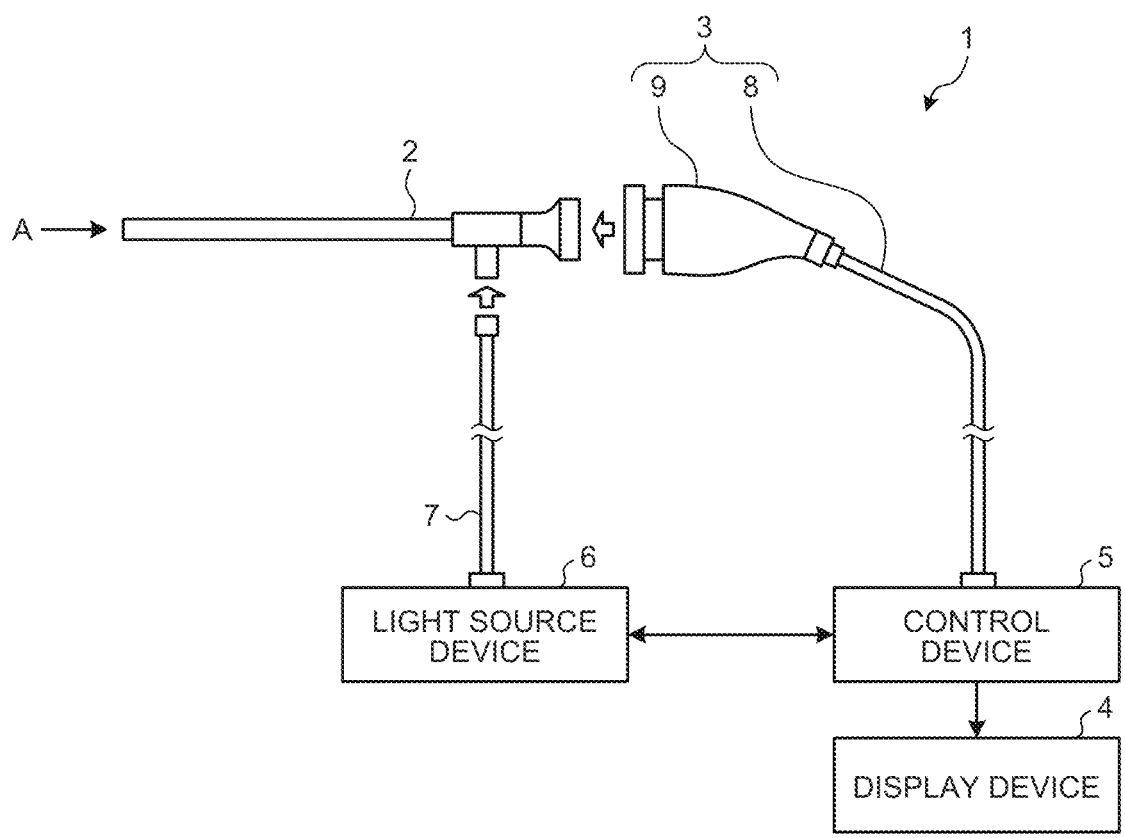
FIG. 1 is a view schematically illustrating a configuration of an endoscope apparatus according to an embodiment.

Hereinafter, modes for carrying out the present disclosure (hereinafter referred to as "embodiments") will be described. In the embodiments, as an example of a medical observation system according to the present disclosure, there will be described a medical endoscope system in which an intra-body image of a subject such as a patient is captured and displayed. Meanwhile, the embodiments do not limit the disclosure in any way. Further, the same components will be described while being denoted by the same reference signs in illustration in the drawings.

EMBODIMENT

FIG. 1 is a view schematically illustrating a configuration of an endoscope system 1 according to an embodiment. The endoscope system 1 is an apparatus that is used in a medical field and observes a subject inside an observed object such as a person (the inside of a living body). The endoscope system 1 includes an endoscope 2, an imaging device 3, a display device 4, a control device 5, and a light source device 6 as illustrated in FIG. 1. The imaging device 3 and the control device 5 form a medical observation system. Additionally, in the present embodiment, the endoscope 2 and the imaging device 3 form an image acquisition apparatus using an endoscope such as a rigid endoscope, for example.

The light source device 6 is connected to one end of a light guide 7 and supplies white light, for example, for illuminating the inside of a living body, to the one end of the light guide 7. Meanwhile, the light source device 6 and the control device 5 may be configured so as to be separated from each other and communicate with each other as illustrated in FIG. 1, or may be configured so as to be integral with each other.

The light guide 7 has one end removably connected to the light source device 6 and has the other end removably connected to the endoscope 2. Then, the light guide 7 transmits light supplied from the light source device 6, from the one end to the other end, and supplies the light to the endoscope 2.

The imaging device 3 captures a subject image provided from the endoscope 2 and outputs a result of the capture. The imaging device 3 includes a transmission cable 8 that is a signal transmission unit, and a camera head 9 as illustrated in FIG. 1. In the present embodiment, the transmission cable 8 and the camera head 9 form a medical imaging apparatus. The imaging device 3 corresponds to an imaging unit.

The endoscope 2 is rigid, has an elongated shape, and is inserted into a living body. In the inside of the endoscope 2, an observation optical system that includes one lens or a plurality of lenses and condenses a subject image is provided. The endoscope 2 emits light supplied via the light guide 7, from a distal end thereof to irradiate the inside of the living body. Then, the light (subject image) applied to the inside of the living body is condensed by the observation optical system in the endoscope 2. The endoscope 2 corresponds to an optical member.

The camera head 9 is removably connected to a proximal end of the endoscope 2 so that the endoscope 2 may rotate. Then, under control of the control device 5, the camera head 9 captures a subject image condensed by the endoscope 2 and outputs an imaging signal obtained through the capture of the subject image. Meanwhile, details of a configuration of the camera head 9 will be provided later.

The transmission cable 8 has one end removably connected to the control device 5 via a connector and has the other end removably connected to the camera head 9 via a connector. More specifically, the transmission cable 8 is a cable in which a plurality of electric wires (not illustrated) are laid inside an outer sheath forming the outermost layer. The plurality of electric wires are electric wires for transmitting an imaging signal output from the camera head 9 to the control device 5 and transmitting a control signal, a synchronizing signal, a clock, and power that are output from the control device 5, to the camera head 9.

The display device 4 displays an image generated by the control device 5 under control of the control device 5. It is preferable that the display device 4 includes a display unit of 55 inches or more in order for an observer to easily get an immersed feeling during observation. However, the size of the display unit is not limited to that.

The control device 5 processes an imaging signal input from the camera head 9 via the transmission cable 8 and outputs an image signal to the display device 4. Further, the control device 5 exercises centralized control over operations of the camera head 9 and the display device 4. Meanwhile, details of a configuration of the control device will be provided later.

Figure 2:
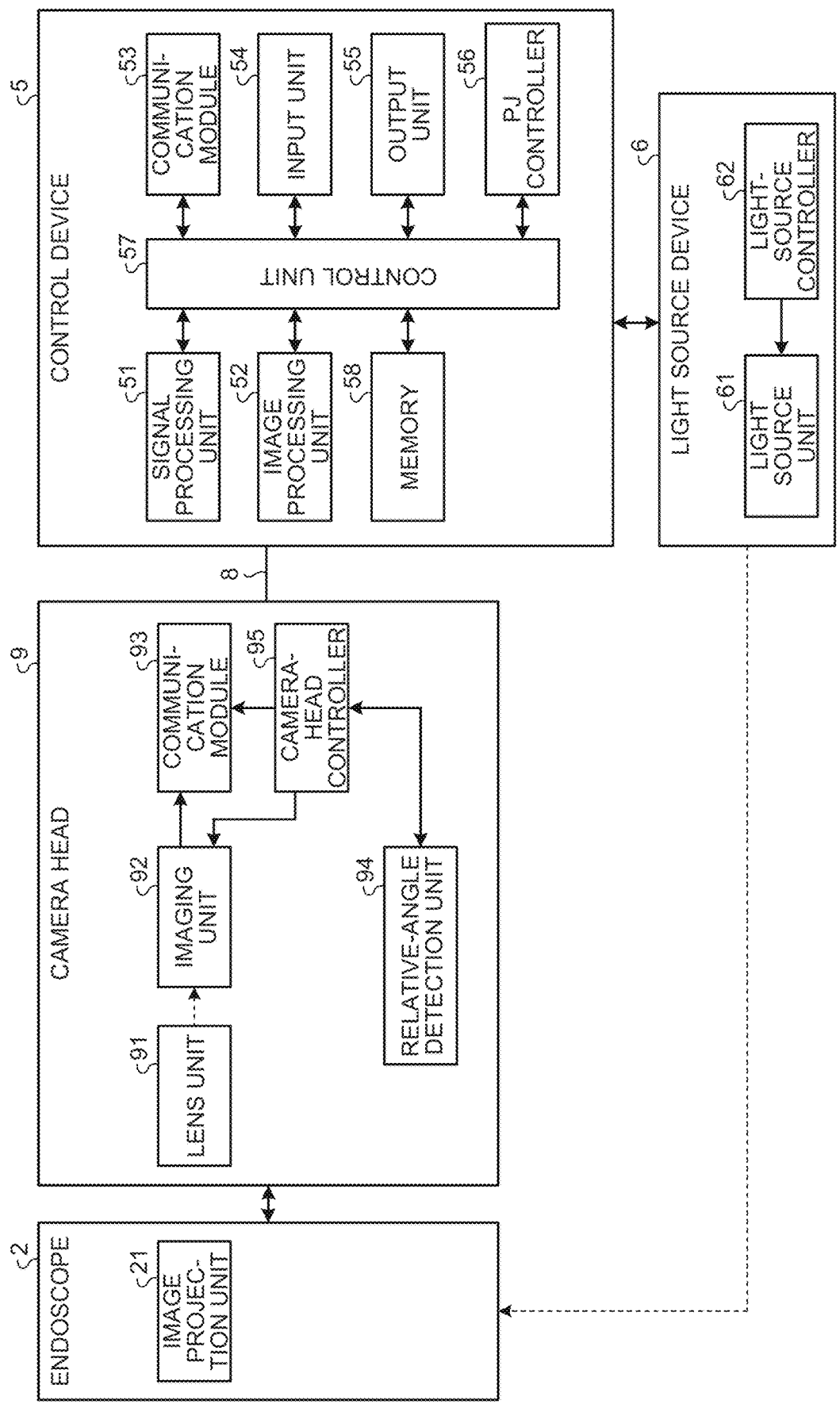
FIG. 2 is a block diagram illustrating configurations of an endoscope, a camera head, a control device, and a light source device that are illustrated in FIG. 1.

Next, configurations of the endoscope 2, the imaging device 3, the control device 5, and the light source device 6 will be described. FIG. 2 is a block diagram illustrating the configurations of the endoscope 2, the camera head 9, the control device 5, and the light source device 6. It is noted that FIG. 2 omits illustration of a connector by which the camera head 9 and the transmission cable 8 are removably connected to each other.

Below, the endoscope 2 (image projection unit 21), a configuration of the control device 5, and a configuration of the camera head 9 will be described in the stated order. Additionally, as the configuration of the control device 5, principal parts of the present disclosure will be chiefly described below.

The endoscope 2 further includes an image projection unit 21 configured to generate a projection image that is an image to be applied externally, in addition to the above-described observation optical system. The image projection unit 21 generates a projection image projected onto a subject, based on an irradiation image transmitted from a PJ controller 56 described later. The image projection unit 21 is supplied with illuminating light from the light source device 6 and projects a projection image onto a subject using the supplied light. The image projection unit 21 includes a projection element such as a digital mirror device (DMD) or a liquid-crystal panel. An adjusting performance of the projection element, in a case of a liquid-crystal panel, for example, is determined by the number of pixels each formed of a set of sub-pixels that transmit red (R) light, green (G) light, and blue (B) light, respectively.

The control device 5 includes a signal processing unit 51, an image processing unit 52, a communication module 53, an input unit 54, an output unit 55, a projector controller (PJ controller) 56, a control unit 57, and a memory 58, as illustrated in FIG. 2. Additionally, the control device 5 may further include a power supply unit (not illustrated) or the like that generates a power-supply voltage for driving the control device 5 and the camera head 9 and supplies the power-supply voltage to respective parts of the control device 5 and to the camera head 9 via the transmission cable 8.

The signal processing unit 51 performs noise removal and signal processing such as A/D conversion as needed, on an imaging signal output from the camera head 9, and outputs a digitized imaging signal (pulse signal) to the image processing unit 52.

Further, the signal processing unit 51 generates a synchronizing signal and a clock for the imaging device 3 and the control device 5. A synchronizing signal (a synchronizing signal that indicates an imaging timing of the camera head 9, or the like, for example) or a clock (a clock for serial communication, for example) for the imaging device 3 is sent through a line not illustrated, to the imaging device 3, which is then driven based on the synchronizing signal or the clock.

The image processing unit 52 generates a displayed image signal displayed on the display device 4, based on an imaging signal input from the signal processing unit 51. The image processing unit 52 performs predetermined signal processing on the imaging signal to generate a displayed image signal including a subject image (captured image). In this regard, the image processing unit 52 performs known image processing including various kinds of image processing such as detection, interpolation, color correction, color enhancement, edge enhancement, and the like. The image processing unit 52 outputs the generated image signal to the display device 4 and also to the PJ controller 56.

The communication module 53 outputs a signal that is received from the control device 5 and includes a later-described control signal transmitted from the control unit 57, to the imaging device 3. Further, the communication module 53 outputs a signal received from the imaging device 3, to respective parts of the control device 5. In other words, the communication module 53 is a relay device that combines signals that are to be output to the imaging device 3 from the respective parts of the control device 5, by parallel-to-serial conversion, for example, and outputs the combined signals, while dividing a signal input from the imaging device 3 by serial-to-parallel conversion, for example, and outputting its resultant signals to respective parts of the control device 5.

The input unit 54 is implemented by using a user interface such as a keyboard, a mouse, or a touch panel, and accepts inputting of various kinds of information.

The output unit 55 is implemented by using a speaker, a printer, a display, or the like, and outputs various kinds of information. The output unit 55 displays an image generated by the image processing unit 52 or outputs an alarm sound or alarm light, under control of the control unit 57.

Figure 3:
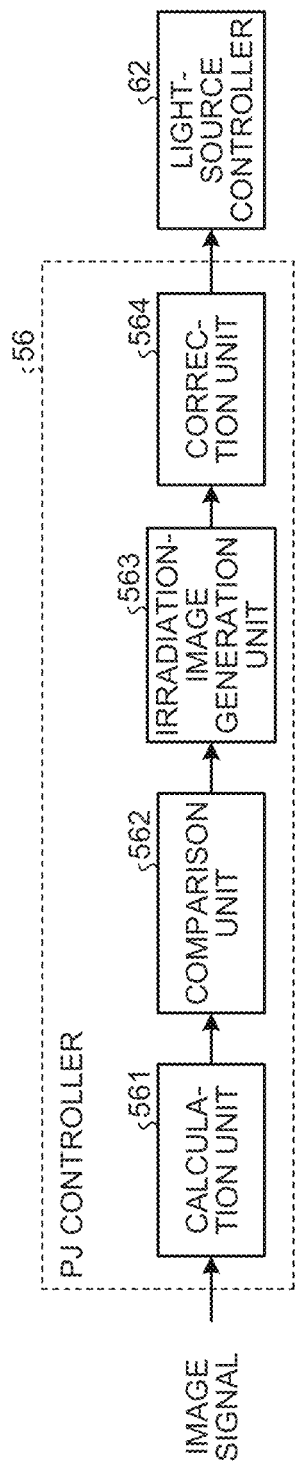
FIG. 3 is a view illustrating a configuration of a PJ controller in the control device illustrated in FIG. 2.

The PJ controller 56 performs conversion on an image signal generated by the image processing unit 52 to generate control information for controlling a light-quantity distribution of illuminating light. The PJ controller 56 generates an irradiation image in which a luminance value or color information is provided in each pixel position, as information about a light-quantity distribution. In the present embodiment, there is generated an irradiation image in which a luminance value is provided in each pixel position. FIG. 3 is a view illustrating a configuration of the PJ controller in the control device illustrated in FIG. 2. The PJ controller 56 includes a calculation unit 561, a comparison unit 562, an irradiation-image generation unit 563, and a correction unit 564.

The calculation unit 561 performs conversion on an image signal and calculates a luminance value in each pixel position. The calculation unit 561 generates a luminance image in which a luminance value is provided in each pixel position, based on the calculated luminance value.

The comparison unit 562 compares a luminance image with a previously-set reference image to generate a difference image. A reference image is an image in which a desired luminance value (reference luminance value) corresponding to a suitable light quantity for irradiation is provided in each pixel position. A difference image is an image in which a difference value in luminance value between a luminance image and a reference image is provided in each pixel position.

The irradiation-image generation unit 563 generates an irradiation image corresponding to a distribution of illuminating light emitted by the light source device 6, based on a difference image. The irradiation-image generation unit 563 extracts a pixel having a difference value exceeding the highest desired value and a pixel having a difference value falling below the lowest desired value with respect to luminance values in the difference image. Here, the highest desired value is a value with respect to a previously-set difference value and corresponds to a first threshold value set based on a difference value by which a light quantity of illuminating light should be reduced. On the other hand, the lowest desired value is a value with respect to a previously-set difference value and corresponds to a second threshold value set based on a difference value by which a light quantity of illuminating light should be increased.

The irradiation-image generation unit 563 subtracts a difference value from a desired luminance value in a reference image for a pixel having a value exceeding the highest desired value among extracted pixels. On the other hand, the irradiation-image generation unit 563 adds a difference value to a desired luminance value in a reference image for a pixel having a value falling below the lowest desired value among extracted pixels.

The irradiation-image generation unit 563 performs subtraction on a desired luminance value for a pixel position with a high luminance value of an acquired image signal and performs addition on a desired luminance value for a pixel position with a low luminance value as described above, thereby generating an irradiation image. An irradiation image includes an area that is darker than a reference image due to reduction of a light quantity in a position (area) with a high luminance value in an image signal and includes an area that is lighter than the reference image due to increase of a light quantity in a position with a low luminance value in the image signal.

The correction unit 564 corrects an irradiation image generated by the irradiation-image generation unit 563. The correction unit 564 corrects an irradiation image in accordance with a positional relationship between the image projection unit 21 of the endoscope 2 and the camera head 9. The correction unit 564 outputs a corrected irradiation image to the image projection unit 21.

More specifically, the PJ controller 56 starts a process of generating an irradiation image when acquiring an image signal. First, the calculation unit 561 calculates a luminance value in each pixel position based on the acquired image signal, to generate a luminance image in which a luminance value is provided in each pixel position. Subsequently, the comparison unit 562 compares the luminance image with a previously-set reference image, to generate a difference image. After generation of the difference image, the irradiation-image generation unit 563 generates an irradiation image corresponding to a light-quantity distribution of illuminating light emitted by the light source device 6, based on the difference image. Thereafter, the correction unit 564 corrects the irradiation image generated by the irradiation-image generation unit 563 and outputs the corrected irradiation image to a light-source controller 62. The image projection unit 21, which has acquired the irradiation image, generates a projection image based on the irradiation image and irradiates a subject with illuminating light having a light-quantity distribution in accordance with the projection image. Thus, a portion having a large quantity of reflected light in the subject is irradiated with a small quantity of illuminating light and a portion having a small quantity of reflected light in the subject is irradiated with a large quantity of illuminating light.

The control unit 57 controls driving of respective components including the control device 5 and the camera head 9, and controls inputting/outputting and the like of information to/from the respective components. The control unit 57 generates a control signal by referring to communication information data (communication format information or the like, for example) stored in the memory 58, and transmits the generated control signal to the imaging device 3 via the communication module 53. Further, the control unit 57 outputs a control signal to the camera head 9 via the transmission cable 8.

The memory 58 is implemented by using a semiconductor memory such as a flash memory, a dynamic random access memory (DRAM), or the like and stores therein communication information data (communication format information or the like, for example). Additionally, the memory 58 may store therein various kinds of programs or the like performed by the control unit 57.

In the meantime, the signal processing unit 51 may include an AF processing unit that outputs a predetermined AF evaluation value of each input frame based on an imaging signal of the input frame, and an AF arithmetic unit that performs AF arithmetic processing for selecting a frame, a focus lens position, or the like that is the most suitable as a focus position, from the AF evaluation values of the frames provided from the AF processing unit.

The above-described components of the signal processing unit 51, the image processing unit 52, the communication module 53, the PJ controller 56, and the control unit 57 are implemented by using either a general-purpose processor such as a central processing unit (CPU) including an internal memory (not illustrated) in which programs are stored, or a dedicated processor that performs a specific function, such as an arithmetic circuit for various operations, typified by an application specific integrated circuit (ASIC). Alternatively, the above-described components may be formed by using a field programmable gate array (FPGA, not illustrated) that is a kind of a programmable integrated circuit. Additionally, in a case of using an FPGA, a memory in which configuration data is stored may be provided so that the FPGA that is a programmable integrated circuit may be configured by using the configuration data read from the memory.

The light source device 6 is connected to one end of the light guide 7, and includes a light source unit 61 that supplies white light, for example, for illuminating the inside of a living body, to the one end of the light guide 7, and the light-source controller 62 that controls emission of illuminating light from the light source unit 61.

Figure 4:
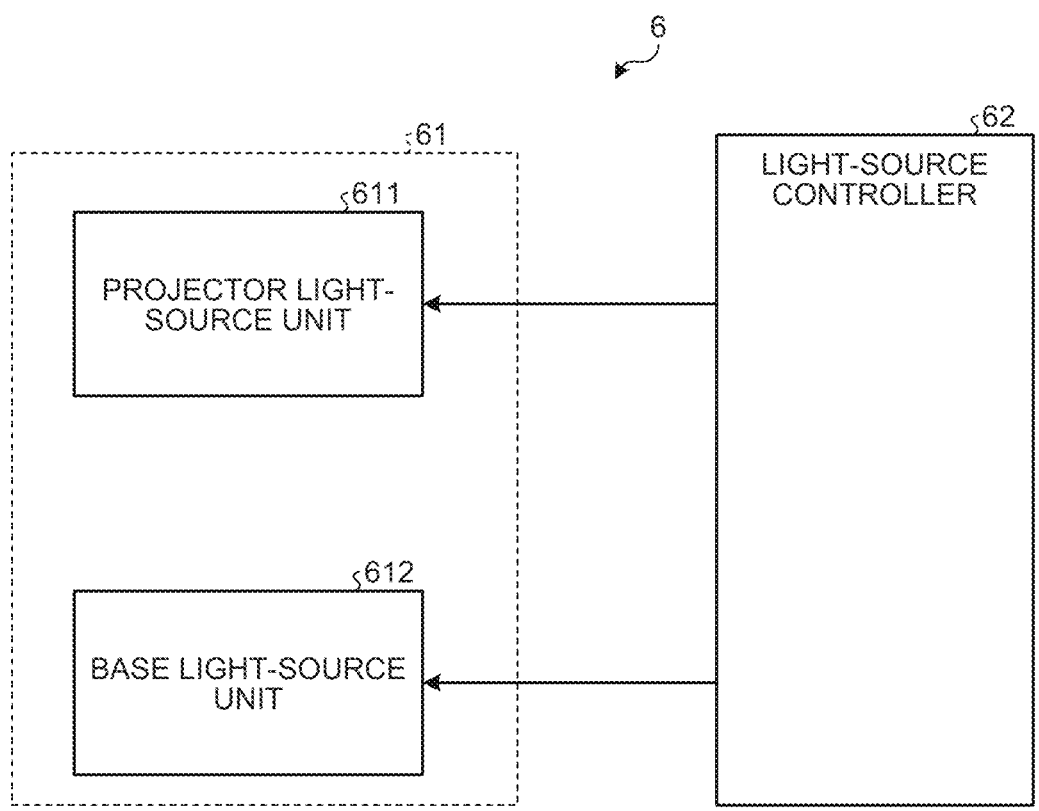
FIG. 4 is a view illustrating a configuration of a light source unit in the light source device illustrated in FIG. 2.

FIG. 4 is a view illustrating a configuration of the light source unit in the light source device illustrated in FIG. 2. The light source unit 61 includes a projector light-source unit 611 and a base light-source unit 612.

The projector light-source unit 611 includes a light source that emits white light supplied to the image projection unit 21 of the endoscope 2, and an optical system that causes white light to be emitted externally. The base light-source unit 612 includes a light source that emits white light and an optical system that causes white light to be emitted externally.

The light source included in the projector light-source unit 611 is formed by using a light source such as a light emitting diode (LED) or a laser diode (LD), for example. The light source included in the base light-source unit 612 is formed by using a light source such as a xenon lamp, a halogen lamp, an LED, or an LD. The light source included in the base light-source unit 612 emits white light having a distribution in accordance with the characteristic of the light source, such as a so-called Gaussian distribution or a top-hat distribution in which a center is placed at an optical axis and a light quantity continuously decreases as a distance from the optical axis increases, for example.

The light-source controller 62 causes the projector light-source unit 611 or the base light-source unit 612 to emit white light, in accordance with an instruction provided from the control unit 57. The image projection unit 21 projects an image (projection image) corresponding to an irradiation image, using the white light of the projector light-source unit 611, so that illuminating light emitted from the light source device 6 has a brightness (light-quantity) distribution corresponding to the irradiation image. Meanwhile, the light-source controller 62 may achieve illumination with normal white light by causing only the base light-source unit 612 to emit white light. Further, both of the respective light sources of the projector light-source unit 611 and the base light-source unit 612 may be caused to emit light.

Next, the principal parts of the present disclosure will be chiefly described as the configuration of the camera head 9. As illustrated in FIG. 2, the camera head 9 includes a lens unit 91, an imaging unit 92, a communication module 93, a relative-angle detection unit 94, and a camera-head controller 95.

The lens unit 91 is formed by using a lens or a plurality of lenses and produces a subject image transmitted through the lens unit 91, onto an imaging surface of an imaging element forming the imaging unit 92. The lens or the plurality of lenses are formed so as to be movable along an optical axis. Then, the lens unit 91 is provided with an optical zoom mechanism (not illustrated) that causes the lens or the plurality of lenses to move to change an angle of view, and a focusing mechanism that changes a focus position. Additionally, the lens unit 91, together with the optical system provided in the endoscope 2, forms an observation optical system that guides observation light incident upon the endoscope 2, to the imaging unit 92.

The imaging unit 92 captures an image of a subject under control of the camera-head controller 95. The imaging unit 92 is formed by using an imaging element that receives a subject image produced by the lens unit 91 and converts the subject image into an electric signal. The imaging element is formed of a charge coupled device (CCD) image sensor or a complementary metal oxide semiconductor (CMOS) image sensor. In a case where the imaging element is a CCD image sensor, a signal processing unit (not illustrated) that performs signal processing (A/D conversion or the like) on an electric signal (analog signal) provided from the imaging element and outputs an imaging signal is mounted in a sensor chip or the like, for example. In a case where the imaging element is a CMOS image sensor, a signal processing unit (not illustrated) that performs signal processing (A/D conversion or the like) on an electric signal (analog signal) obtained by conversion of light into an electric signal and outputs an imaging signal is included in the imaging element, for example. The imaging unit 92 outputs the generated electric signal to the communication module 93.

It is preferable that the number of pixels in an image sensor of the imaging unit 92 is equal to the number of pixels in a projection element of the light source unit 61.

The communication module 93 outputs a signal transmitted from the control device 5, to respective parts such as the camera-head controller 95 in the camera head 9. Further, the communication module 93 converts information about a current state of the camera head 9, or the like, into a form of a signal complying with a previously-determined transmission method, and outputs the signal obtained by the conversion, to the control device 5 via the transmission cable 8. In other words, the communication module 93 is a relay device that divides a signal input from the control device 5 or the transmission cable 8 by serial-to-parallel conversion or the like, for example, and outputs resultant signals to the respective parts of the camera head 9, while combining and outputting signals that are provided from the respective parts of the camera head 9 and are to be output to the control device 5 and the transmission cable 8, by parallel-to-serial conversion, for example.

The relative-angle detection unit 94 detects information about a relative angle of the endoscope 2 mounted onto the camera head 9. From information detected by the relative-angle detection unit 94, a correction value (rotation angle) of an irradiation image generated by the PJ controller 56 relative to an angle of view of an image captured by the camera head 9 is obtained. A detection result provided by the relative-angle detection unit 94 is output to the control device 5. This angle detection performed by the relative-angle detection unit 94 will be described later.

The camera-head controller 95 controls operations of the whole of the camera head 9 in accordance with a driving signal input via the transmission cable 8 or with an instruction signal or the like that is output from an operating unit such as a switch provided so as to be exposed in an outer surface of the camera head 9, through a user's operation on the operating unit. Further, the camera-head controller 95 outputs information about a current state of the camera head 9 to the control device 5 via the transmission cable 8.

The above-described components of the communication module 93 and the camera-head controller 95 are implemented by using either a general-purpose processor such as a CPU including an internal memory (not illustrated) in which programs are stored, or a dedicated processor that performs a specific function, such as an arithmetic circuit for various operations, typified by an ASIC. Alternatively, the above-described components may be formed by using an FPGA that is a kind of a programmable integrated circuit. Additionally, in a case of using an FPGA, a memory in which configuration data is stored may be provided so that the FPGA that is a programmable integrated circuit may be configured by using the configuration data read from the memory.

Alternatively, in the camera head 9 or the transmission cable 8, there may be formed a signal processing unit that performs signal processing on an imaging signal generated by the communication module 93 or the imaging unit 92. Further, an imaging clock for driving the imaging unit 92 and a control clock for the camera-head controller 95 that are generated based on a reference clock generated by an oscillator (not illustrated) provided in the camera head 9 may be output to the imaging unit 92 and the camera-head controller 95, respectively. Moreover, timing signals for various kinds of processing in the imaging unit 92 and the camera-head controller 95 may be generated based on a synchronizing signal input from the control device 5 via the transmission cable 8 and be output to the imaging unit 92 and the camera-head controller 95, respectively. Additionally, the camera-head controller 95 may be provided in the transmission cable 8 or the control device 5, instead of the camera head 9.

In the above-described endoscope system 1, an image that is based on an electric signal and is captured by the imaging unit 92 is displayed on the display device 4. At the same time, an image signal displayed on the display device 4 is input to the PJ controller 56 and feedback control of the light source device 6 is performed. Examples of feedback control of the light source device 6 include control of a light quantity in the base light-source unit 612 and the like.

The above-described illumination control may be exercised either every time an image signal is input or per several frames.

Figure 5:
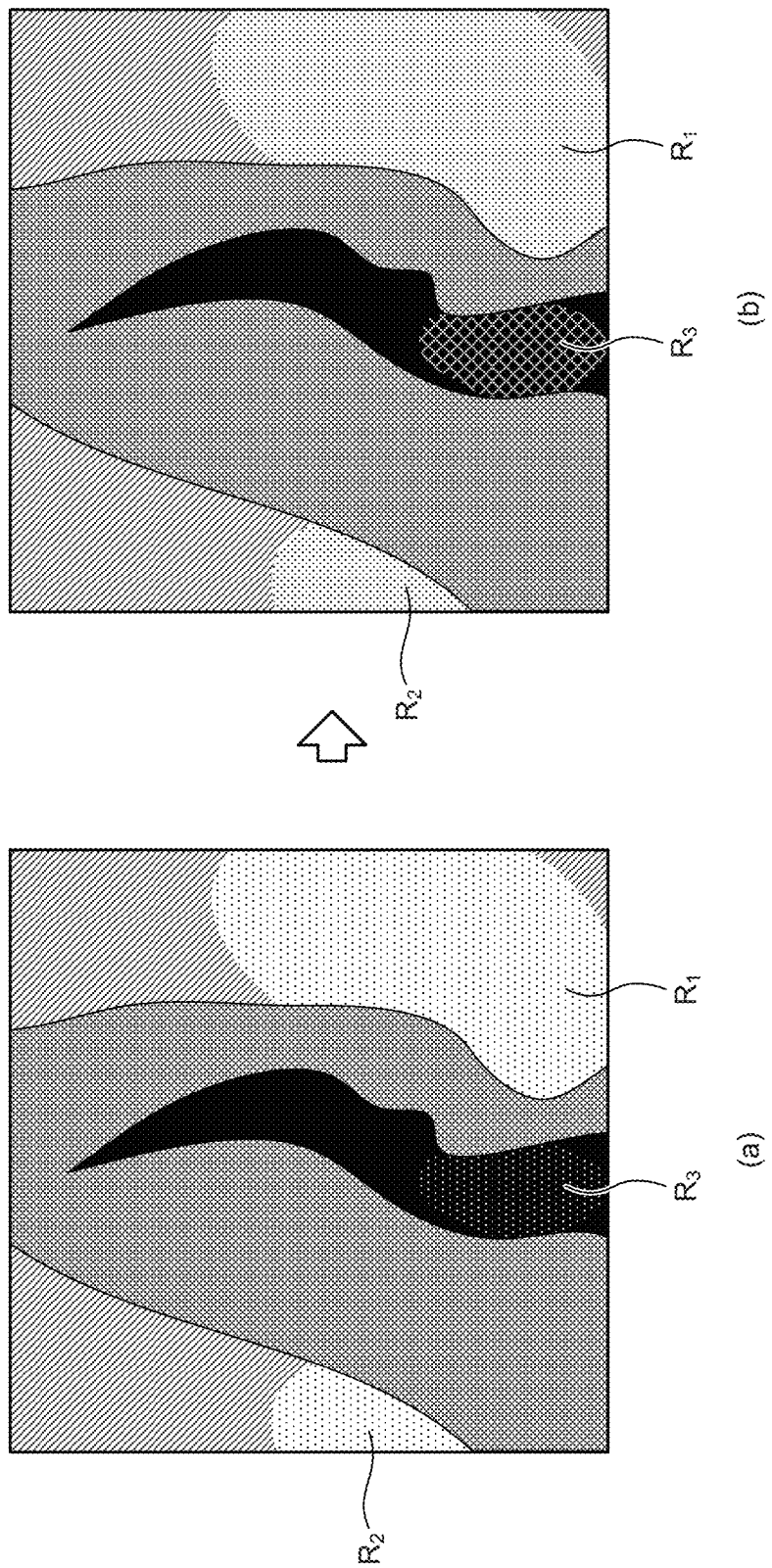
FIG. 5 is a view schematically illustrating examples of images before and after emission control of illuminating light.

FIG. 5 is a view schematically illustrating examples of images before and after emission control of illuminating light. (a) of FIG. 5 illustrates an image before emission control of a uniform quantity of illuminating light. (b) of FIG. 5 illustrates an image after emission control of illuminating light using an irradiation image. (a) and (b) of FIG. 5 both illustrate captured images of the same lumen. As illustrated in (a) of FIG. 5, before emission control, there is provided an image in which blown-out highlights occur in areas R1 and R2 on a near-point side in the lumen and blocked-up shadows occur in an area R3 on a far-point side. In this case, under control of the light-source controller 62 and by referring to the image illustrated in (a) of FIG. 5, illuminating light of which light quantity is reduced on a near-point side (the areas R1 and R2) and is increased on a far-point side (the area R3) is emitted. As a result of this, after emission control as illustrated in (b) of FIG. 5, there is acquired an image in which brightness on a near-point side is reduced and brightness on a far-point side is increased.

Figure 6:
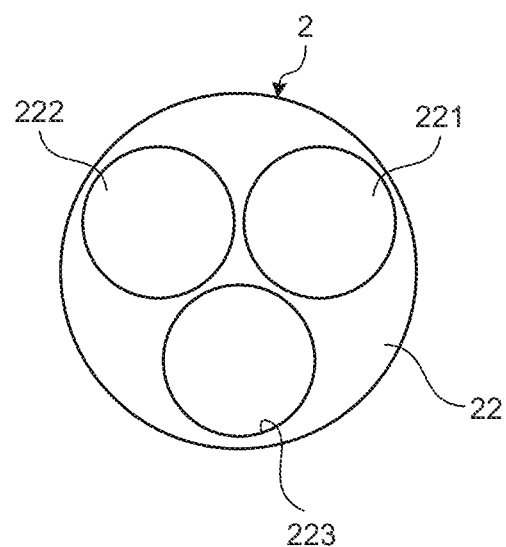
FIG. 6 is a view illustrating a configuration of a distal end of the endoscope when seen from a direction of an arrow A in FIG. 1.

Here, a correcting process performed by the correction unit 564 of the PJ controller 56 will be described with reference to FIG. 6 to FIG. 15. FIG. 6 is a view illustrating a configuration of a distal end of the endoscope when seen from a direction of an arrow A in FIG. 1. The endoscope 2 includes, at the distal end thereof, an image irradiation unit 221 that emits a light image that corresponds to an irradiation image and is generated by the image projection unit 21, an illumination irradiation unit 222 that emits illuminating light supplied from the base light-source unit 612, and a light reception unit 223 that receives light from a subject and takes it into the endoscope 2. In the present embodiment, the center of the image irradiation unit 221 and the center of a projection image projected by the image projection unit 21 coincide with each other.

Figure 7:
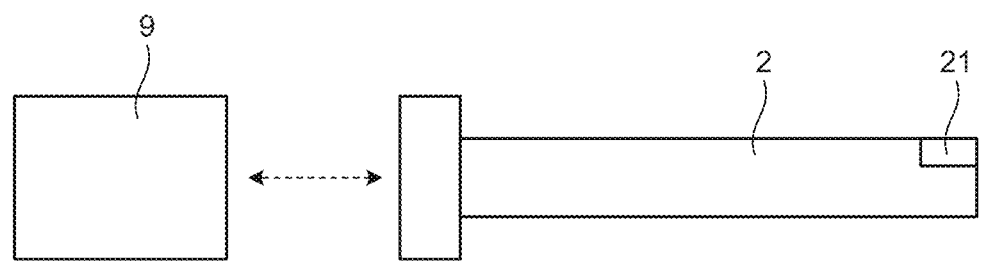
FIG. 7 is a view (first example) illustrating a positional relationship between an image projection unit of the endoscope and the camera head.
Figure 8:
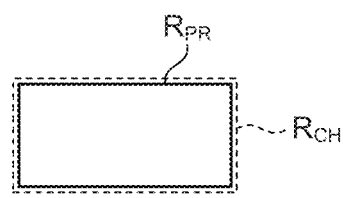
FIG. 8 is a view for explaining a captured area of an irradiation image transmitted to the endoscope from the camera head and a projected area of a projection image generated by the image projection unit in a case where the positional relationship illustrated in FIG. 7 is established.

FIG. 7 is a view (first example) illustrating a positional relationship between the image projection unit of the endoscope and the camera head. FIG. 8 is a view for explaining a captured area of an irradiation image transmitted to the endoscope from the camera head and a projected area of an irradiation image generated by the image projection unit in a case where the positional relationship illustrated in FIG. 7 is established. FIG. 7 is a view illustrating a state in which a projected area of a projection image projected by the image projection unit 21 and a captured area captured by the imaging unit 92 of the camera head 9 coincide with each other.

When an angle of view of an irradiation image transmitted to the image projection unit 21 coincides with a captured area of the imaging unit 92 of the camera head 9, a projected area $R_{PR}$ of a projection image in a case where an irradiation image generated by an irradiation-image generation unit 563 is projected onto a subject overlaps a captured area $R_{CH}$ captured by the camera head 9. Thus, the projection image in a case where an irradiation image is projected onto the subject coincides with a corresponding position in the subject in an image captured by the camera head 9 (refer to FIG. 8).

Figure 9:
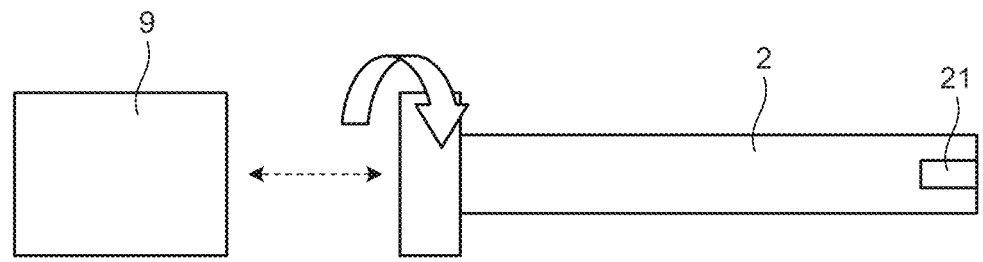
FIG. 9 is a view (second example) illustrating a positional relationship between the image projection unit of the endoscope and the camera head.
Figure 10:
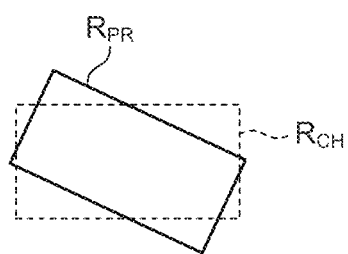
FIG. 10 is a view for explaining a captured area of an irradiation image transmitted to the endoscope from the camera head and a projected area of a projection image generated by the image projection unit in a case where the positional relationship illustrated in FIG. 9 is established.

FIG. 9 is a view (second example) illustrating a positional relationship between the image projection unit of the endoscope and the camera head. FIG. 10 is a view for explaining a captured area of an irradiation image transmitted to the endoscope from the camera head and a projected area of an irradiation image generated by the image projection unit in a case where the positional relationship illustrated in FIG. 9 is established. The endoscope 2 may rotate about a longitudinal axis of the endoscope 2 while being connected to the camera head 9. FIG. 9 is a view illustrating a state in which the endoscope 2, which has been placed in the state as illustrated in FIG. 7, rotates relative to the camera head 9 and a projected area of a projection image projected by the image projection unit 21 is displaced relative to a captured area captured by the imaging unit 92 of the camera head 9.

Deviation of an angle of view of an irradiation image transmitted to the image projection unit 21 from an angle of view of an image captured by the imaging unit 92 of the camera head 9 causes the projected area $R_{PR}$ of a projection image in a case where an irradiation image generated by an irradiation-image generation unit 563 is projected onto a subject, to be displaced relative to the captured area $R_{CH}$ captured by the camera head 9. Thus, the projection image in a case where an irradiation image is projected onto a subject is displaced relative to a corresponding position in the subject in the image captured by the camera head 9 (refer to FIG. 10).

Displacement of the endoscope 2 and the camera head 9 relative to each other is detected by the relative-angle detection unit 94, as a rotation angle of the endoscope 2 (image projection unit 21) relative to the camera head 9. In the present embodiment, a position of rotation of the center of the image irradiation unit 221 that emits a projection image of the image projection unit 21, relative to a reference position (reference position P B described later) is detected.

Figure 11:
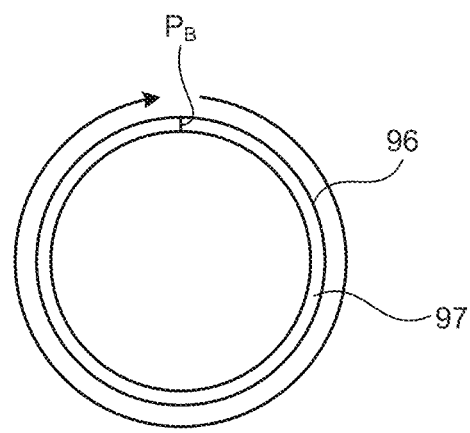
FIG. 11 is a view illustrating examples of components included in the camera head, in a configuration that detects a rotation angle of the endoscope relative to the camera head.
Figure 12:
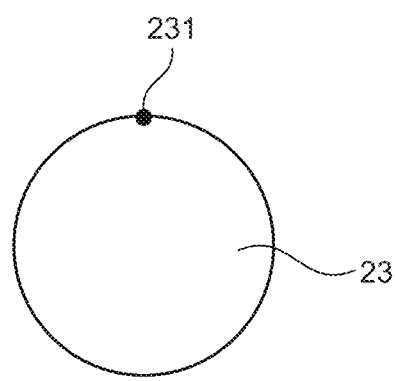
FIG. 12 is a view illustrating examples of components included in the endoscope, in the configuration that detects a rotation angle of the endoscope relative to the camera head.

FIG. 11 is a view illustrating examples of components included in the camera head, in a configuration that detects a rotation angle of the endoscope relative to the camera head. FIG. 12 is a view illustrating examples of components included in the endoscope, in the configuration that detects a rotation angle of the endoscope relative to the camera head. In the camera head 9, a connecting unit 96 for connection to the endoscope 2 is provided with a resistance unit 97 that has resistance varying with a connection position of the endoscope 2. On the other hand, in the endoscope 2, a connecting unit 23 for connection to the camera head 9 is provided with a terminal unit 231 that comes into contact with the resistance unit 97 when connected to the camera head 9. In the resistance unit 97, a resistance value to be obtained upon contact with the terminal unit increases as the resistance unit 97 moves away from a position to be referred (reference position), in a predetermined rotation direction (refer to an arrow in FIG. 11).

When the camera head 9 is connected to the endoscope 2, a position of contact of the terminal unit 231 with the resistance unit 97 varies with a position of rotation of the endoscope 2 relative to the reference position P B in the camera head 9. Further, in a case where the endoscope 2 is caused to rotate relative to the camera head 9 during use, a position of contact of the terminal unit 231 with the resistance unit 97 varies. There is obtained a resistance value that varies in accordance with a position of contact of the terminal unit 231 with the resistance unit 97, depending on a position (rotation position) of the endoscope 2 relative to the camera head 9.

Figure 13A:
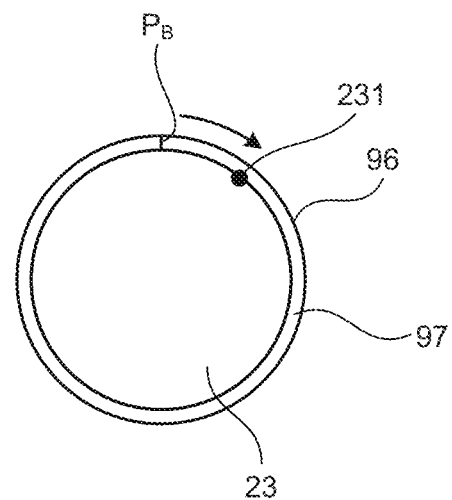
FIG. 13A is a view illustrating an example (first example) of connection between the endoscope and the camera head.
Figure 13B:
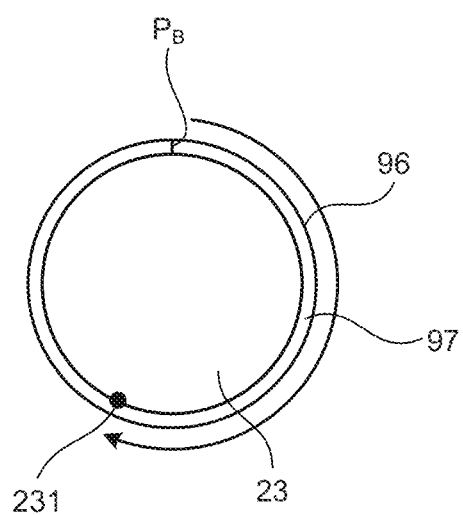
FIG. 13B is a view illustrating an example (second example) of connection between the endoscope and the camera head.

FIGS. 13A and 13B are views illustrating examples of connection between the endoscope and the camera head. Due to variation in a rotation position of the endoscope 2 relative to the camera head 9, resistance values to be respectively obtained in states illustrated in FIG. 13A and FIG. 13B are different from each other. More specifically, a resistance value to be obtained in the state illustrated in FIG. 13B in which the position of contact is farther from the reference position P B is higher than a resistance value to be obtained in the state illustrated in FIG. 13A.

Figure 14:
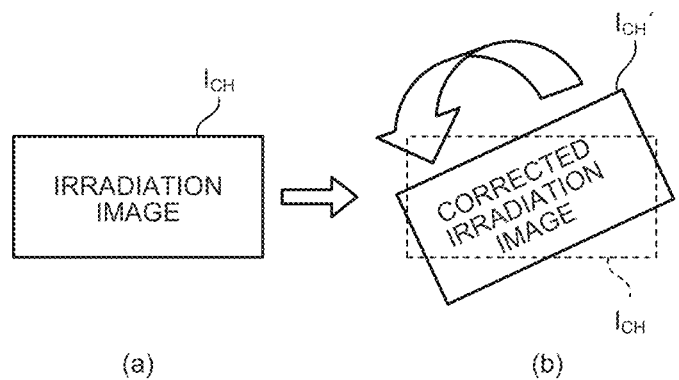
FIG. 14 is a view for roughly explaining a flow of a correcting process performed by a correction unit of the PJ controller.

FIG. 14 is a view for roughly explaining a flow of the correcting process performed by the correction unit of the PJ controller. When it is determined from a detection result provided by the relative-angle detection unit 94, that the endoscope 2 (image projection unit 21) rotates relative to the reference position and correction is necessary, the correction unit 564 corrects an irradiation image based on the detection result. When it is determined that correction is necessary, the correction unit 564 rotates an irradiation image $I_{CH}$ generated by the irradiation-image generation unit 563, to generate a corrected irradiation image $I_{CH}'$, based on the detection result.

Figure 15:
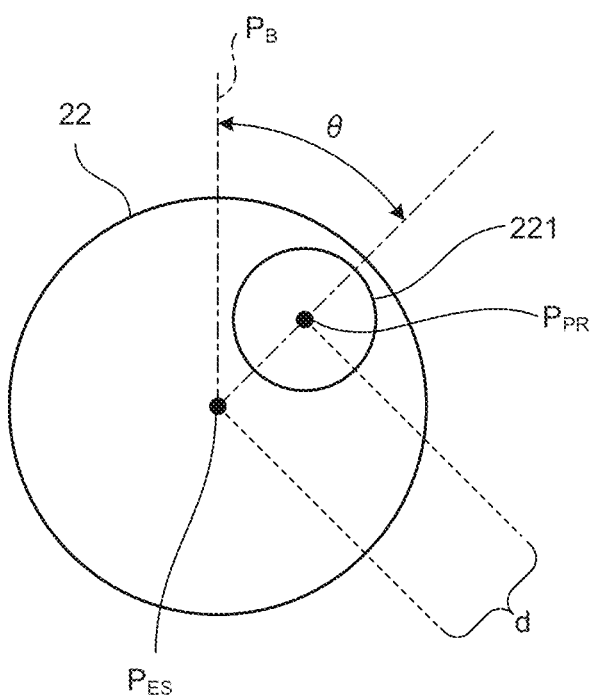
FIG. 15 is a view for explaining the correcting process performed by the correction unit of the PJ controller.

FIG. 15 is a view for explaining the correcting process performed by the correction unit of the PJ controller. The correction unit 564 calculates a rotation angle θ of the center $P_{PR}$ of the image irradiation unit 221 (image projection unit 21) relative to the reference position $P_B$, from a detection result (resistance value) provided by the relative-angle detection unit 94. Subsequently, the correction unit 564, using a distance d between a center PEs of the endoscope 2 that is previously measured and stored in the memory 58 and the center $P_{PR}$ of the image irradiation unit 221 and the calculated rotation angle θ, rotates the irradiation image $I_{CH}$ by the rotation angle θ about the center PES on a virtual circle that has the center $P_{ES}$ as its center and has the radius d passing through the center $P_{PR}$ and the reference position $P_B$, thereby correcting the irradiation image $I_{CH}$. Additionally, the longitudinal axis of the endoscope 2 passes through the center $P_{ES}$ of the endoscope 2. Further, an optical axis of the observation optical system of the endoscope 2 passes through the center of a captured area of the imaging unit 92. In FIG. 15, the longitudinal axis of the endoscope 2 extends along a direction perpendicular to the drawing sheet.

The image projection unit 21 generates a projection image corresponding to the obtained irradiation image ICH' and projects the projection image onto a subject, thereby achieving illumination using the projection image in accordance with the subject in a captured area captured by the camera head 9.

According to the above-described embodiment, feedback of a captured image is performed, and the image projection unit 21 provided in the endoscope 2 generates a projection image based on an irradiation image in which a light quantity in a position with a high luminance value is reduced while a light quantity in a position with a low luminance value is increased. Then, an image corresponding to the projection image is used as illuminating light for irradiation of a subject, which enables fine control of a light-quantity distribution of illuminating light with which a subject is irradiated.

Further, according to the above-described embodiment, an irradiation image is corrected in accordance with a rotation angle of the endoscope 2 relative to a reference position (reference position P B) in the camera head 9. This corrects displacement between an image captured by the camera head 9 and a projection image projected as illuminating light, which enables more accurate control of a light-quantity distribution of illuminating light with which a subject is irradiated.

(Modification)

Figure 16:
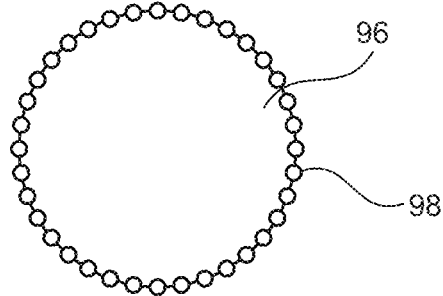
FIG. 16 is a view illustrating different examples of components included in the camera head, in a configuration that detects a rotation angle of the endoscope relative to the camera head according to a modification.
Figure 17:
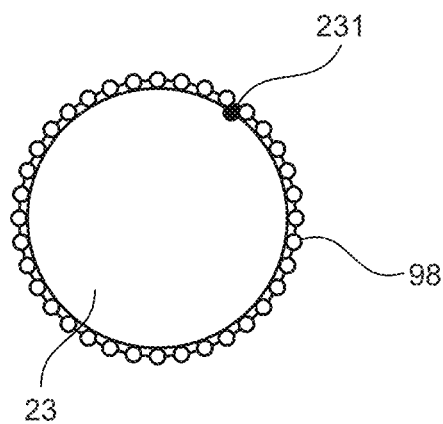
FIG. 17 is a view illustrating an example of connection between the endoscope and the camera head.

Next, a modification of the embodiment will be described. FIG. 16 is a view illustrating different examples of components included in the camera head, in a configuration that detects a rotation angle of the endoscope relative to the camera head, according to the modification. FIG. 17 is a view illustrating different examples of components included in the endoscope, in the configuration that detects a rotation angle of the endoscope relative to the camera head, according to the modification. The modification is different from the embodiment in components provided in the camera head for detecting a relative angle. The modification is the same as the endoscope system 1 of the above-described embodiment in the other respects than the foregoing components, and thus description is accordingly omitted.

In the camera head 9, the connecting unit 96 for connection to the endoscope 2 is provided with a plurality of terminal units 98 (second terminal units) arranged along an outer edge. On the other hand, in the endoscope 2, the connecting unit 23 for connection to the camera head 9 is provided with a terminal unit 231 (first terminal unit) that is connected to any of the terminal units 98 when connected to the camera head 9 (refer to FIG. 17).

When the endoscope 2 is connected to the camera head 9, electrical conduction is caused between the terminal unit 231 of the endoscope 2 and one of the terminal units 98 that has come into contact with the terminal unit 231, so that the terminal unit 98 in contact with the terminal unit 231 is designated. The conducting terminal unit 98 is detected by the relative-angle detection unit 94.

FIG. 17 is a view illustrating an example of connection between the endoscope and the camera head. The terminal unit 98 in contact with the terminal unit 231 varies with a change in a rotation position of the endoscope 2 relative to the camera head 9. The correction unit 564 calculates the rotation angle θ of the image irradiation unit 221 (image projection unit 21) relative to the reference position $P_B$, from a detection result (the designated terminal unit 98) provided by the relative-angle detection unit 94 (refer to FIG. 15). Subsequently, the correction unit 564, using the distance d between the center $P_{ES}$ of the endoscope 2 that is previously measured and stored in the memory 58 and the center $P_{PR}$ of the image irradiation unit 221 and the calculated rotation angle θ, rotates the irradiation image $I_{CH}$ by the rotation angle θ about the center $P_{ES}$ on a virtual circle that has the center $P_{ES}$ as its center and has the radius d passing through the center $P_{PR}$ and the reference position $P_B$, thereby correcting the irradiation image $I_{CH}$.

The above-described modification also may produce the same effects as those in the above-described embodiment.

Other Embodiments

Next, other embodiments will be described. For example, a comparison unit 562, using a luminance value or the like calculated by a calculation unit 561, identifies a treatment tool in an image through edge detection or the like and extracts a contour of the treatment tool. An irradiation-image generation unit 563 generates an irradiation image in which the inside of the extracted treatment tool is set as an area not irradiated with illuminating light. This prevents the treatment tool from being irradiated with illuminating light, thereby acquiring an image in which blown-out highlights due to reflected light from the treatment tool are suppressed.

Further, for example, the comparison unit 562, using a luminance value or the like calculated by the calculation unit 561, compares color information in an area with previously-stored information about an organ to detect the organ, through edge detection or based on a relation between magnitudes of luminance values, and extracts an area where the organ is present. The irradiation-image generation unit 563 generates an irradiation image that is divided into a first area, i.e., the extracted area, where the organ is present and a second area where the organ is absent. The PJ controller 56 causes light in different wavelength ranges to be emitted toward the first area and the second area, respectively. For example, an area corresponding to the first area is irradiated with white light and an area corresponding to the second area is irradiated with light (blue light or green light, for example) in a wavelength range different from that of white light. In this case, it is preferable that a projection element is a liquid-crystal panel. Further, it is preferable that illuminating light with which the first area is irradiated is light in a wavelength range by which an organ is clearly colored. This makes it possible to acquire an image that allows easy identification of an organ.

Alternatively, with a bleeding area extracted from an image, illuminating light for the bleeding area may be controlled such that the bleeding area is irradiated with light in a wavelength range by which blood or tissue in a bleeding portion is so colored as to be easily identified on the image.

Further alternatively, with bacteria extracted from an image, illuminating light for an area where the bacteria is present may be controlled such that the area is irradiated with light in a wavelength range by which the bacteria is so colored as to be easily identified on the image.

Meanwhile, though observation with white light has been described as an example in the above-described embodiments, the disclosure may be applied also to special-light observation such as fluorescence observation using exciting light. For example, it is possible to regulate a range of exciting-light irradiation or regulate a light quantity of exciting light by the above-described control of a light quantity of illuminating light.

In a case where the disclosure is applied to special-light observation, the projector light-source unit 611 includes a light source that emits special light. The light source of special light is a light source that emits special light (exciting light, for example) when applied to special-light observation. In this regard, special light corresponds to light in a wavelength range that copes with any of the following kinds of special-light observations. The PJ controller 56 generates an irradiation image in which an irradiation area is formed only in a portion desired to be excited in a subject, which enables exciting-light irradiation of only the portion desired to be exited. Additionally, a portion desired to be excited may be designated by an operator in a captured image, or be extracted by the above-described contour extraction or the like.

For example, in a case where an irradiation image is generated from a fluorescent image that is a kind of a special-light image, first, the whole of an irradiation area is irradiated with exciting light, to acquire a fluorescent image. Subsequently, the calculation unit 561 calculates a luminance value in each pixel position in the fluorescent image to generate a luminance image in which a luminance value is provided in each pixel position. Then, the comparison unit 562 extracts a pixel having a luminance value higher than a threshold value in the luminance image. The irradiation-image generation unit 563 generates an irradiation image in which an area formed of an extracted pixel is set as an area to be irradiated with exciting light. The threshold value at that time corresponds to a third threshold value that is set to a value equal to or higher than a luminance value corresponding to a low-luminance noise and lower than a lower limit of a luminance value corresponding to fluorescence intensity.

Examples of special-light observations include: NBI in which narrow-range illuminating light having central wavelengths of 415 nm and 540 nm is applied and states of blood vessels in a mucous-membrane surface layer and a layer deeper than that are observed by using a difference in absorption into hemoglobin between the light having the above-stated wavelengths; IRI in which medicine called Indocyanine green (ICG) having an absorption peak in near-infrared light having a wavelength of approximately 805 nm in blood is injected intravenously as a contrast medium, exciting light having a central wavelength of approximately 805 nm is applied, and fluorescence from ICG is observed, to determine presence or absence of blood streams; AFI in which a fluorescent agent is previously administered to a subject, a fluorescent image emitted from the subject due to exciting-light irradiation thereof is observed, and presence or absence, as well as a shape, of the fluorescent image is observed to examine a tumor; and PDD. A solution of amino levulinic acid (5-ALA), which would be metabolized by a raw material of blood (heme) in a normal tissue in a body when taken by a patient, is not metabolized by a cancer cell but is accumulated as an intermediate called PpIX. The intermediate PpIX has a property of fluorescing in red (having a peak wavelength of 630 nm) when irradiated with blue light (having a central wavelength of 410 nm). In PDD, by using this property of PpIX, an image that allows easy distinction between a cancer cell and a normal cell is acquired.

Further, in photodynamic therapy (PDT), with a treatment range determined, light may be controlled such that only the treatment range is irradiated with the light.

Further, though a rigid endoscope has been described as an example of an optical member in the above-described embodiments, a flexible endoscope may be employed or an exoscope may be employed.

While the modes for carrying out the present disclosure have been described above, the present disclosure should not be limited only to the above-described embodiments. Though it has been described that the control device 5 performs signal processing and the like in the above-described embodiments, the processing may be performed by components in the camera head 9.

Additionally, it has been described that the relative-angle detection unit 94 detects a rotation angle based on a value in accordance with a position of physical contact between the endoscope 2 and the camera head 9. Alternatively, for example, a rotation angle may be detected by projection and capture of an irradiation image generated by the irradiation-image generation unit 563 and calculation of a rotation angle of an angle of view of the irradiation image relative to an angle of view of the captured image. In this alternative, the relative-angle detection unit 94 extracts an angle of view of the irradiation image in the captured image. In this irradiation image for calculation of a rotation angle, there may be put a mark (an image showing a corner defined by an angle of view, for example) for extracting an angle of view.

Further, though the example in which the PJ controller 56 is provided in the control device 5 has been described in the above-described embodiments, the PJ controller 56 may be provided in the light source device 6. Moreover, though the example in which the relative-angle detection unit 94 is provided in the camera head 9 has been described in the above-described embodiments, the relative-angle detection unit 94 may be provided in the control device 5.

Further, though the example in which the light source unit 61 includes the projector light-source unit 611 and the base light-source unit 612 has been described in the above-described embodiments, the light source unit 61 may be configured so as to include only the projector light-source unit 611.

Additionally, the present technique may have the following configuration also.

(1) A medical control apparatus including
circuitry configured to:
generate an irradiation image represented by illuminating-light irradiation, based on a brightness distribution of a captured image captured by an imaging device; and
control generation of a projection image and projection of the projection image onto a subject by an image projector provided in an optical member based on the irradiation image and a rotation angle for rotation of the optical member rotatably connected to the imaging device about a longitudinal axis of the optical member relative to the imaging device.

(2) The medical control apparatus according to (1), wherein the rotation angle is a rotation angle of the image projector relative to a reference position set in a connector to which the optical member is connected in the imaging device.

(3) The medical control apparatus according to (2), wherein the rotation angle is calculated based on a resistance value obtained in accordance with a position of contact between a terminal provided in a connector for connection to the imaging device in the optical member and a resistor that is provided in the connector to which the optical member is connected in the imaging device and has a resistance value varying with a position of contact with the terminal.

(4) The medical control apparatus according to (2), wherein the rotation angle is calculated based on a position of a second terminal out of a plurality of second terminals provided in the connector to which the optical member is connected in the imaging device, the second terminal being in contact with a first terminal provided in a connector for connection to the imaging device in the optical member.

(5) The medical control apparatus according to any one of (1) to (4), wherein the circuitry is configured to:
convert the captured image into a luminance image in which a luminance value is provided in each pixel; and
generate the irradiation image in which a projection luminance of an area having the luminance value higher than a first threshold value is made lower than a previously-set reference luminance and a projection luminance of an area having the luminance value lower than a second threshold value is made higher than the reference luminance.

(6) The medical control apparatus according to any one of (1) to (5), wherein the circuitry is configured to:
convert a special-light image that is captured by the imaging device using special light, into a luminance image in which a luminance value is provided in each pixel; and
generate the irradiation image in which an area having the luminance value higher than a third threshold value in the luminance image is set as an exciting-light irradiation area.

(7) A medical observation system including:
an optical member having an elongated shape, the optical member being configured to condense a subject image and emit supplied light from a distal end;
an imaging device connected to the optical member such that the optical member is removable and rotatable about a longitudinal axis of the optical member, the imaging device being configured to capture the subject image condensed by the optical member;
circuitry configured to
generate a captured image based on an electric signal generated through capture by the imaging device,
detect a rotation angle of the optical member for rotation about the longitudinal axis relative to the imaging device,
generate an irradiation image that indicates a distribution of a light quantity of illumination light based on a distribution of the light quantity in accordance with a brightness distribution of the captured image,
correct the irradiation image in accordance with the rotation angle;
a light source configured to supply light to the optical member; and
an image projector provided in the optical member, the image projector being configured to generate a projection image based on the irradiation image having been corrected by the circuitry and project the projection image onto a subject.

(8) The medical observation system according to (7), wherein the circuitry is configured to detect a rotation angle of the image projector relative to a reference position set in a connector to which the optical member is connected in the imaging device.

(9) The medical observation system according to (8), wherein
the optical member includes
a first connector configure to connect the imaging device, and
a terminal provided in the first connector, the imaging device includes
a second connector to which the optical member is connected, and
a resistor having a resistance value varying with a position of contact with the second terminal, and
the circuitry is configured to detect a rotation angle of the image projector based on the resistance value obtained in accordance with the position of contact between the second terminal and the resistor.

(10) The medical observation system according to (8), wherein
the optical member includes
a first connector configured to connect the imaging device, and
a first terminal provided in the connector, the imaging device includes
a second connector to which the optical member is connected, and
a plurality of second terminals provided in the second connector, at least one of the plurality of second terminals being in contact with the first terminal, and
the circuitry is configured to detect a rotation angle of the image projector based on a position of a second terminal out of the plurality of second terminals, the second terminal being in contact with the first terminal.

(11) The medical observation system according to any one of (7) to (10), further including
an output unit configured to display the captured image generated by the circuitry.

The present disclosure produces effects of finely controlling a light-quantity distribution of illuminating light with which a subject is irradiated.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control apparatus for use with an image projector, that receives light from a light source and generates a projection image; and an optical member to provide the projection image to a subject and provide an image of the subject to an imaging sensor, the image projector and the optical member being rotatably coupled to the imaging sensor about a longitudinal axis of the optical member, the medical control apparatus comprising
circuitry configured to:
generate the image of the subject illuminated by the projection image based on a brightness distribution of a captured image captured by the imaging sensor; and
control generation of the projection image and projection of the projection image onto the subject, based on the image projector being rotatable about the longitudinal axis of the optical member relative to the imaging sensor.

2. The medical control apparatus according to claim 1, wherein the circuitry is configured to control generation of the projection image and projection of the projection image onto the subject, based on a rotation angle of the image projector relative to a reference position set in a connector to which the optical member is connected to the imaging sensor.

3. The medical control apparatus according to claim 2, wherein the rotation angle is calculated based on a resistance value obtained in accordance with a position of contact between a terminal provided in a connector for connection to the imaging sensor in the optical member and a resistor that is provided in the connector to which the optical member is connected to the imaging sensor and has a resistance value varying with a position of contact with the terminal.

4. The medical control apparatus according to claim 2, wherein the rotation angle is calculated based on a position of a second terminal out of a plurality of second terminals provided in the connector to which the optical member is connected to the imaging sensor, the second terminal being in contact with a first terminal provided to a connector for connection to the imaging sensor in the optical member.

5. The medical control apparatus according to claim 1, wherein the circuitry is configured to:
convert the captured image into a luminance image in which a luminance value is provided in each pixel; and
generate the image in which a projection luminance of an area having the luminance value higher than a first threshold value is made lower than a previously-set reference luminance and a projection luminance of an area having the luminance value lower than a second threshold value is made higher than the previously-set reference luminance.

6. The medical control apparatus according to claim 1, wherein the circuitry is configured to:
convert a special-light image, that is captured by the imaging sensor when the subject is illuminated using special light, into a luminance image in which a luminance value is provided in each pixel; and
generate the image in which an area having the luminance value higher than a third threshold value in the luminance image is set as an exciting-light irradiation area.

7. A medical observation system comprising:
a light source configured to supply light;
an image projector that receives light from the light source and generates a projection image;
an optical member having an elongated shape, the optical member being configured to provide the projection image to a subject and transmit an image of the subject;
an imaging sensor coupled to the optical member and the image projector such that the optical member and the image projector are rotatable about a longitudinal axis of the optical member, the imaging sensor being configured to capture the subject image from the optical member; and
circuitry configured to
generate a captured image based on an electric signal generated through capture by the imaging sensor,
detect a rotation angle of the optical member for rotation about the longitudinal axis relative to the imaging sensor,
generate an irradiation image that indicates a distribution of a light quantity of illumination light based on a distribution of the light quantity in accordance with a brightness distribution of the captured image, and
correct the irradiation image in accordance with the rotation angle, based on the image projector being rotatable about a longitudinal axis of the optical member relative to the imaging sensors.

8. The medical observation system according to claim 7, wherein the circuitry is configured to detect a rotation angle of the image projector relative to a reference position set in a connector to which the optical member is connected in to imaging sensor.

9. The medical observation system according to claim 8, wherein
the optical member includes
a first connector configured to connect to the imaging sensor, and
a terminal provided in the first connector,
the imaging sensor includes
a second connector to which the optical member is connected, and
a resistor having a resistance value varying with a position of contact with the terminal, and
the circuitry is configured to detect a rotation angle of the image projector based on the resistance value obtained in accordance with the position of contact between the terminal and the resistor.

10. The medical observation system according to claim 8, wherein
the optical member includes
a first connector configured to connect to the imaging sensor, and
a first terminal provided in the first connector,
the imaging sensor includes
a second connector to which the optical member is connected, and
a plurality of second terminals provided in the second connector, at least one of the plurality of second terminals being in contact with the first terminal, and
the circuitry is configured to detect a rotation angle of the image projector based on a position of the at least one of the plurality of second terminals out of the plurality of second terminals, the at least one of the plurality of second terminals being in contact with the first terminal.

11. The medical observation system according to claim 7, further comprising
a display configured to display the captured image generated by the circuitry.

12. The medical observation system according to claim 7, wherein the circuitry is configured to:
convert the captured image into a luminance image in which a luminance value is provided in each pixel; and
generate the irradiation image in which a projection luminance of an area having the luminance value higher than a first threshold value is made lower than a previously-set reference luminance and a projection luminance of an area having the luminance value lower than a second threshold value is made higher than the previously-set reference luminance.

13. The medical observation system according to claim 7, wherein the circuitry is configured to:
convert a special-light image, that is captured by the imaging sensor when the subject is illuminated using special light, into a luminance image in which a luminance value is provided in each pixel; and
generate the irradiation image in which an area having the luminance value higher than a third threshold value in the luminance image is set as an exciting-light irradiation area.

14. A medical control method for use with an image projector, that receives light from a light source and generates a projection image, and an optical member to provide the projection image to a subject and provide an image of the subject to an imaging sensor, the image projector and the optical member being rotatably coupled to the imaging sensor about a longitudinal axis of the optical member, the medical control method comprising
generating the image of the subject illuminated by the projection image based on a brightness distribution of a captured image captured by the imaging sensor; and
controlling generation of the projection image and projection of the projection image onto the subject, based on the image projector being rotatable about the longitudinal axis of the optical member relative to the imaging sensor.

15. The medical control method according to claim 14, wherein the controlling generation of the projection image and projection of the projection image onto the subject is based on a rotation angle of the image projector relative to a reference position set in a connector to which the optical member is connected to the imaging sensor.

16. The medical control method according to claim 15, further comprising calculating the rotation angle based on a resistance value obtained in accordance with a position of contact between a terminal provided in a connector for connection to the imaging sensor in the optical member and a resistor in the connector to which the optical member is connected to the imaging sensor and has a resistance value varying with a position of contact with the terminal.

17. The medical control method according to claim 15, further comprising calculating the rotation angle based on a position of a second terminal out of a plurality of second terminals provided in the connector to which the optical member is connected in the imaging sensor, the second terminal being in contact with a first terminal provided in a connector for connection to the imaging sensor in the optical member.

18. The medical control method according to claim 14, further comprising:
 converting the captured image into a luminance image in which a luminance value is provided in each pixel; and
 generating the image in which a projection luminance of an area having the luminance value higher than a first threshold value is made lower than a previously-set reference luminance and a projection luminance of an area having the luminance value lower than a second threshold value is made higher than the previously-set reference luminance.

19. The medical control method according to claim 14, further comprising:
 converting a special-light image, that is captured by the imaging sensor using special light, into a luminance image in which a luminance value is provided in each pixel; and
 generating the image in which an area having the luminance value higher than a third threshold value in the luminance image is set as an exciting-light irradiation area.

* * * * *